(12) United States Patent  
Yoon et al.

(10) Patent No.: US 11,069,061 B2
(45) Date of Patent: Jul. 20, 2021

(54) METHOD AND APPARATUS FOR CALCULATING ABDOMINAL DISEASE DIAGNOSIS INFORMATION BASED ON MEDICAL IMAGE

(71) Applicant: Wonkwang University Center for Industry-Academy Cooperation, Jeollabuk-do (KR)

(72) Inventors: Kwon Ha Yoon, Jeollabuk-do (KR); Ji Eon Kim, Jeju-do (KR); Tae Hoon Kim, Jeollabuk-do (KR); Si Hyung No, Jeollabuk-do (KR); Chung Sub Lee, Jeollabuk-do (KR); Seung Jin Kim, Jeollanam-do (KR); Chang Won Jeong, Jeollabuk-do (KR)

(73) Assignee: WONKWANG UNIVERSITY CENTER FOR INDUSTRY-ACADEMY COOPERATION, Jeollabuk-Do (KR)

( * ) Notice: Subject to any disclaimer, the term of this patent is extended or adjusted under 35 U.S.C. 154(b) by 58 days.

(21) Appl. No.: 16/527,808

(22) Filed: Jul. 31, 2019

(65) Prior Publication Data
US 2020/0143532 A1     May 7, 2020

(30) Foreign Application Priority Data
Nov. 7, 2018    (KR) .......................... 10-2018-0135772

(51) Int. Cl.
*G06T 7/13*     (2017.01)
*A61B 8/00*     (2006.01)
*G06T 7/00*     (2017.01)
*A61B 6/00*     (2006.01)
*A61B 5/00*     (2006.01)

(52) U.S. Cl.
CPC .............. *G06T 7/0012* (2013.01); *G06T 7/13* (2017.01); *A61B 5/7485* (2013.01); *A61B 6/469* (2013.01); *A61B 8/469* (2013.01); *G06T 2207/30056* (2013.01)

(58) Field of Classification Search
None
See application file for complete search history.

(56) References Cited

U.S. PATENT DOCUMENTS

| 2012/0083005 A1* | 4/2012 | Malecki | G01N 33/6857 435/7.23 |
| 2017/0046839 A1* | 2/2017 | Paik | G06K 9/00147 |
| 2020/0143532 A1* | 5/2020 | Yoon | G06T 7/0012 |

FOREIGN PATENT DOCUMENTS

KR     10-1018960 B1     3/2011

* cited by examiner

*Primary Examiner* — Tahmina N Ansari
(74) *Attorney, Agent, or Firm* — The PL Law Group, PLLC (57) ABSTRACT

A method for analyzing an abdominal disease based on a medical image, includes receiving and preprocessing a medical image obtained by photographing an abdominal region of a patient to detect a plurality of analysis candidate regions and setting one of the plurality of analysis candidate regions as a ROI, calculating a nodule grade based on surface unevenness of the ROI, calculating a cellular heterogeneity coefficient based on pixel homogeneity of the ROI, and predicting and outputting an abdominal disease value based on the nodule grade and the cellular heterogeneity coefficient.

7 Claims, 8 Drawing Sheets

METHOD AND APPARATUS FOR CALCULATING ABDOMINAL DISEASE DIAGNOSIS INFORMATION BASED ON MEDICAL IMAGE

CROSS-REFERENCE TO RELATED APPLICATION AND CLAIM OF PRIORITY

This application claims priority to Korean Patent Application No. 10-2018-0135772 filed on Nov. 7, 2018 in the Korean Intellectual Property Office (KIPO), the entire disclosure of which is incorporated by reference herein.

This study was supported by the grants of the National Research Foundation of Korea (NRF) (2016M3A9A7918501) and the Korea Health Technology R&D Project through the Korea Health Industry Development Institute (KHIDI), funded by the Ministry of Health & Welfare (HI18C1216).

BACKGROUND

1. Technical Field

This disclosure relates to a method and apparatus for analyzing an abdominal disease based on a medical image, and in particular, to a method and apparatus for analyzing an abdominal disease based on a medical image, which calculates a nodule grade and a cellular heterogeneity coefficient from a medical image obtained by photographing an abdominal region of a patient and simply predicts and notifies the degree of abdominal disease by using the nodule grade and the cellular heterogeneity coefficient.

2. Background Art

As a blood vessel for supplying oxygen-rich blood, about a quarter of the blood flow of the whole body circulates through the liver. Also, the portal vein serves to supply nutrient-rich blood from the intestines. The liver serves to supply and store the ingested food as an energy source for the body, synthesizes proteins, and releases ammonia, which is a metabolite of protein, to prevent accumulation of toxins in the body. In addition, cooper cells present in the liver suppress the growth of bacteria in the body through phagocytosis to serve as a defense line of the body. In this way, the liver is one of the most important organs with hundreds of functions.

If the liver is repeatedly damaged due to factors such as frequent drinking or virus invasion, the corresponding site is hardened to suffer from fibrosis. Hepatocirrhosis and cirrhosis are liver diseases caused by the fibrosis. If hepatitis recurs repeatedly to develop chronic hepatitis, it develops into hepatocirrhosis and leads to liver cancer within several years.

The liver fibrosis index is used as an important index to check the liver health status of the patients. Currently, it is possible to check the liver fibrosis index by using an ELF (Enhanced Liver Fibrosis) device and a liver fibrosis scanning device.

The ELF device is designed to measure the degree of liver fibrosis by measuring and analyzing hyaluronic acid (HA), aminoterminal propeptide of type III procollagen, and tissue inhibitor of metalloproteinase 1 (TIMP-1), which are components of the ECM (extracellular matrix).

The liver fibrosis scanning device is a device for checking the degree of liver fibrosis by placing a probe composed of a vibrator and an ultrasonic transducer between the ribs near the liver and then measuring the velocity of an elastic wave.

Meanwhile, a medical staff checks a liver image of the patient obtained through an imaging device such as CT or MRI by naked eyes and additionally checks the degree of liver fibrosis using the ELF device and the liver fibrosis scanning device only if the liver disease is suspected, thereby finally diagnosing the degree of disease of the patient.

Namely, in the conventional art, in order to accurately check the liver health of a patient, an image analysis process using a CT, an MRI and an ultrasound imaging device and a liver fibrosis checking process using the ELF device and the liver fibrosis scanning device must be performed together, which however unnecessarily increases the cost and time required for diagnosing the degree of disease of the patient.

SUMMARY

This disclosure is to solve the above problems, and the present disclosure is directed to providing a new-type method and apparatus for analyzing an abdominal disease based on a medical image, which may calculate a nodule grade and a cellular heterogeneity coefficient from a medical image obtained by photographing an abdominal region of a patient and simply predict and notify the degree of abdominal disease by using the nodule grade and the cellular heterogeneity coefficient.

The objects of the present disclosure are not limited to the above, and other objects not mentioned herein may be clearly understood by those skilled in the art from the following description.

In one general aspect, there is provided a method for calculating abdominal disease diagnosis information based on a medical image, comprising: receiving and preprocessing a medical image obtained by photographing an abdominal region of a patient to detect a plurality of analysis candidate regions and setting one of the plurality of analysis candidate regions as a ROI (Region Of Interest); calculating a nodule grade based on surface unevenness of the ROI; calculating a cellular heterogeneity coefficient based on pixel homogeneity of the ROI; and predicting and outputting an abdominal disease value based on the nodule grade and the cellular heterogeneity coefficient.

The step of calculating a nodule grade may include: extracting a border line of the ROI; selecting a partial line of the border line as a nodule-concerned line based on a user input value; linearly interpolating the nodule-concerned line by performing polynomial curve-fitting regression analysis to the nodule-concerned line; and calculating and statistically analyzing a distance deviation between the nodule-concerned line and the border line to calculate the nodule grade.

The step of calculating a cellular heterogeneity coefficient may include: selecting a partial or entire region of the ROI as an analysis target region based on a user input value; and calculating a cellular heterogeneity coefficient based on brightness values of pixels in the analysis target region.

In another aspect of the present disclosure, there is also provided an apparatus for analyzing an abdominal disease based on a medical image, comprising: a medical image preprocessing unit configured to detect a plurality of analysis candidate regions by receiving and preprocessing a medical image obtained by photographing an abdominal region of a patient; a ROI selecting unit configured to set one of the plurality of analysis candidate regions as a ROI; a nodule grade calculating unit configured to calculate a nodule grade based on surface unevenness of the ROI; a cellular heterogeneity coefficient calculating unit configured to calculate a cellular heterogeneity coefficient based on pixel homogeneity of the ROI; and a disease analyzing unit configured to predict and output the degree of abdominal disease based on the nodule grade and the cellular heterogeneity coefficient.

In the present disclosure, it is possible to calculate a nodule grade and a cellular heterogeneity coefficient from a medical image obtained by photographing an abdominal region of a patient and simply predicts and notifies the degree of abdominal disease by using the nodule grade and the cellular heterogeneity coefficient. In this case, since the degree of abdominal disease of the patient may be predicted and notified simultaneously with the acquisition of the medical image, it is possible to greatly reduce the cost and time required for diagnosing the degree of disease of the patient.

DETAILED DESCRIPTION

The objects and effects of the present disclosure and the technical features for achieving them will become apparent with reference to the embodiments described in detail below along with the accompanying drawings. In the following description of the present disclosure, known functions or configurations will not be described in detail when it is determined that the gist of the present disclosure may be unnecessarily obscured thereby.

In addition, the following terms are defined in consideration of the functions in the present disclosure and may vary depending on the intention of a user or an operator, or the customs.

However, the present disclosure is not limited to the embodiments disclosed below, but may be implemented in various other ways. The embodiments are provided just for perfect explanation of the present disclosure and for allowing those of skilled in the art to completely understand the present disclosure, and the present disclosure is defined only by the scope of the claims. Therefore, the definition should be based on the contents throughout the specification.

Figure 1:
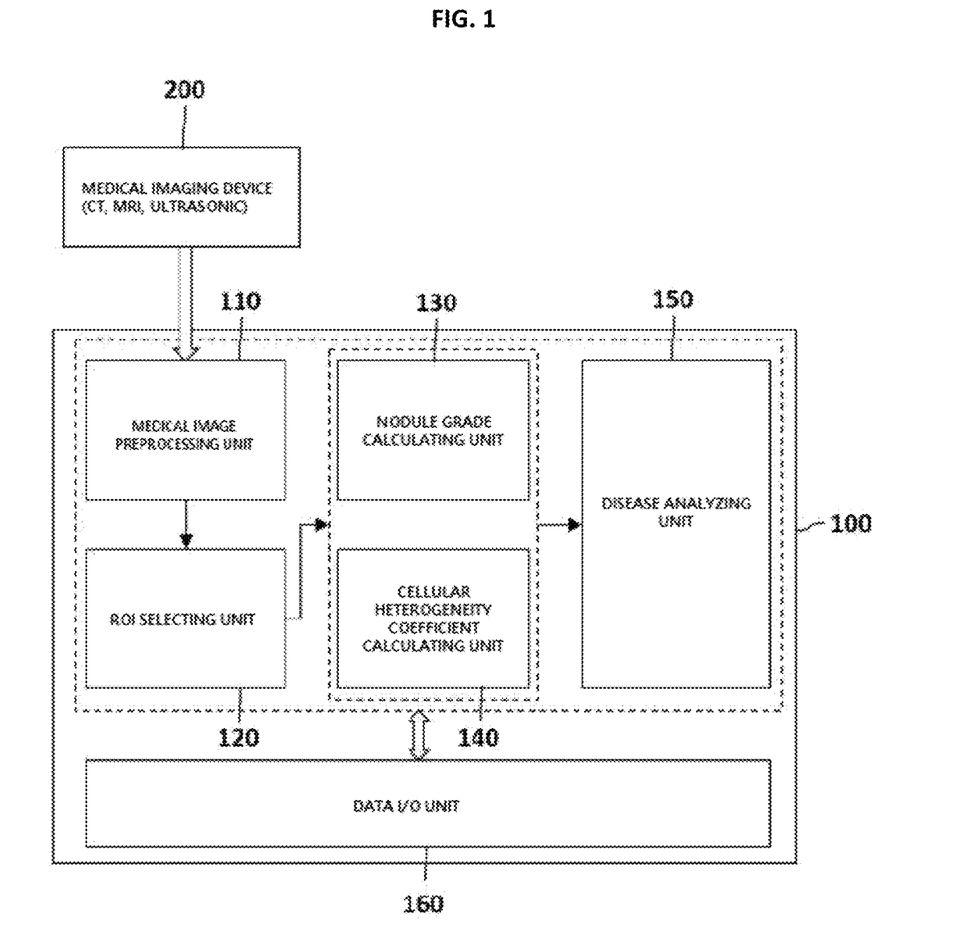
FIG. 1 is a diagram showing an apparatus for analyzing an abdominal disease based on a medical image according to an embodiment of the present disclosure.

FIG. 1 is a diagram showing an apparatus for analyzing an abdominal disease based on a medical image (hereinafter, also referred to as an "abdominal disease analyzing apparatus") according to an embodiment of the present disclosure.

Referring to FIG. 1, the abdominal disease analyzing apparatus 100 according to the present disclosure includes a medical image preprocessing unit 110 for receiving a medical image, obtained by photographing an abdominal region of a patient, from a medical imaging device 200 such as a CT (Computed Tomography) device, an MRI (Magnetic Resonance Imaging) device, and an ultrasonic device and preprocessing the medical image, a ROI (Region Of Interest) selecting unit 120 for extracting an ROI based on the preprocessed medical image, a nodule grade calculating unit 130 for calculating a nodule grade based on surface unevenness of the ROI, a cellular heterogeneity coefficient calculating unit 140 for calculating a cellular heterogeneity coefficient based on pixel homogeneity of the ROI, a disease analyzing unit 150 for acquiring and storing analysis criterion information in which correlations of the nodule grade, the cellular heterogeneity coefficient and the degree of abdominal disease are defined in advance and predicting and outputting the degree of abdominal disease corresponding to the nodule grade and the cellular heterogeneity coefficient based on the analysis criterion information, and a data I/O unit 160 for receiving a user control value or outputting a current operating state of the apparatus in an audiovisual manner.

Figure 2:
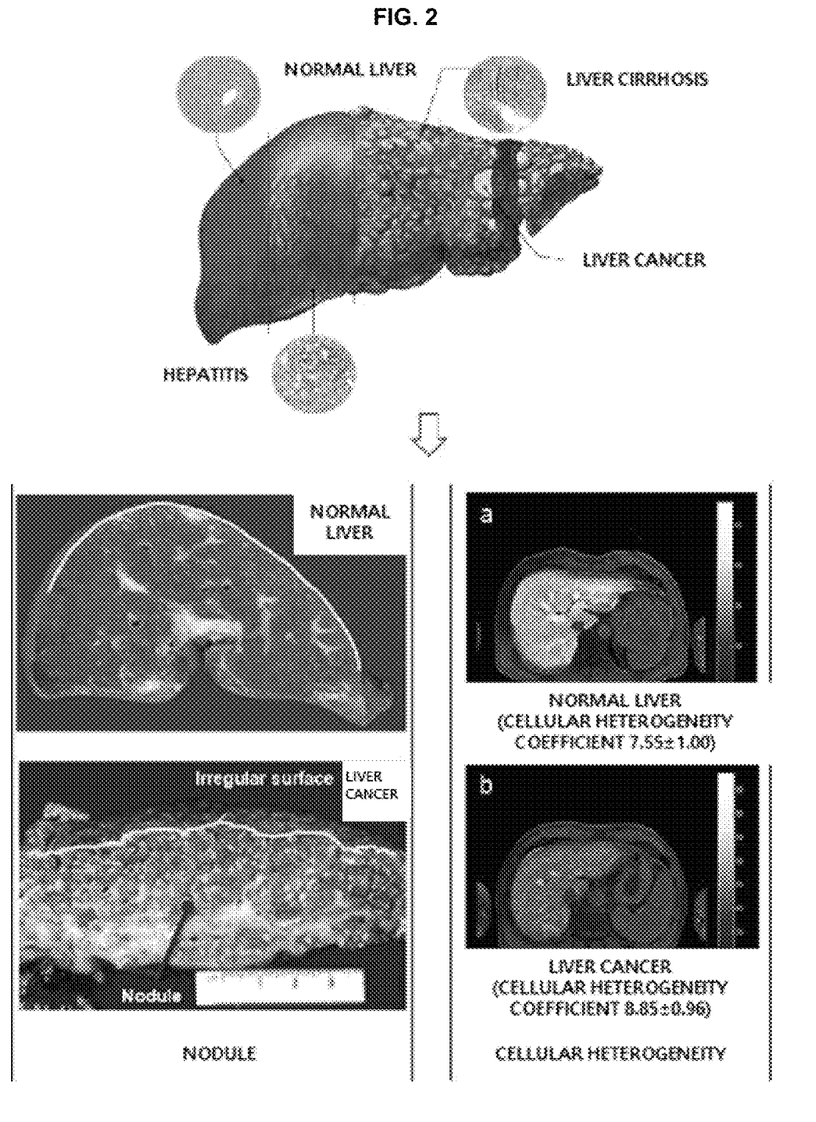
FIG. 2 is a diagram showing a body change pattern according to a liver disease.

For reference, as shown in FIG. 2, in case of abdominal diseases such as liver disease, if the degree of disease becomes more serious, the degree of nodule formation increases, and also the number of atypical cells in the diseased area also increases.

Thus, in the present disclosure, a nodule grade reflecting the degree of nodule formation and a cellular heterogeneity coefficient reflecting the number of atypical cells in the diseased area is calculated based on a medical image, and then the degree of abdominal disease of a patient is automatically predicted and guided by utilizing these parameters.

Hereinafter, an abdominal disease analyzing method according to the present disclosure will be described in detail with reference to FIGS. 3 to 8.

Figure 3:
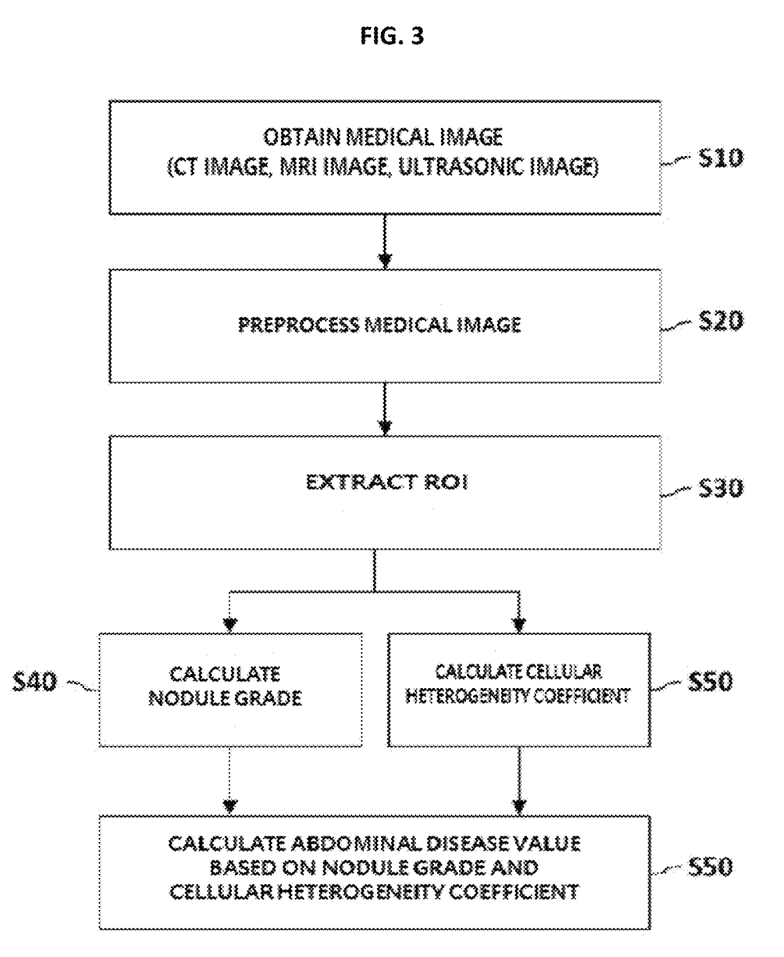
FIG. 3 is a flowchart for illustrating a whole abdominal disease analyzing method according to an embodiment of the present disclosure.
Figure 4:
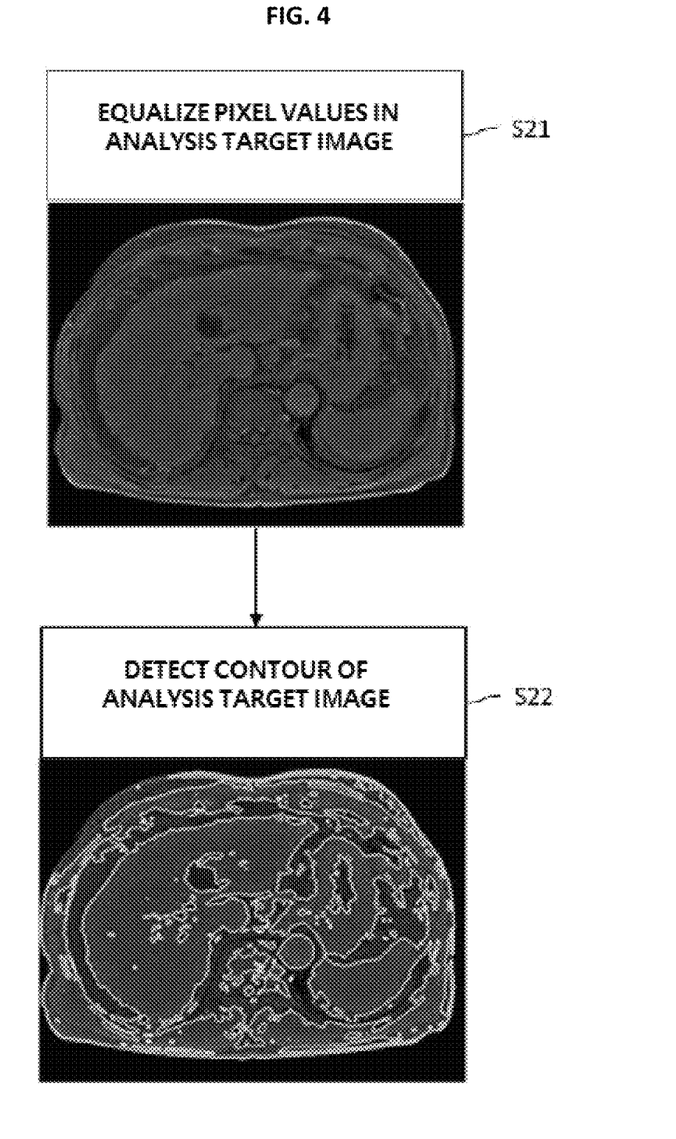
FIG. 4 is a detailed flowchart for illustrating a medical image preprocessing step according to an embodiment of the present disclosure.
Figure 5:
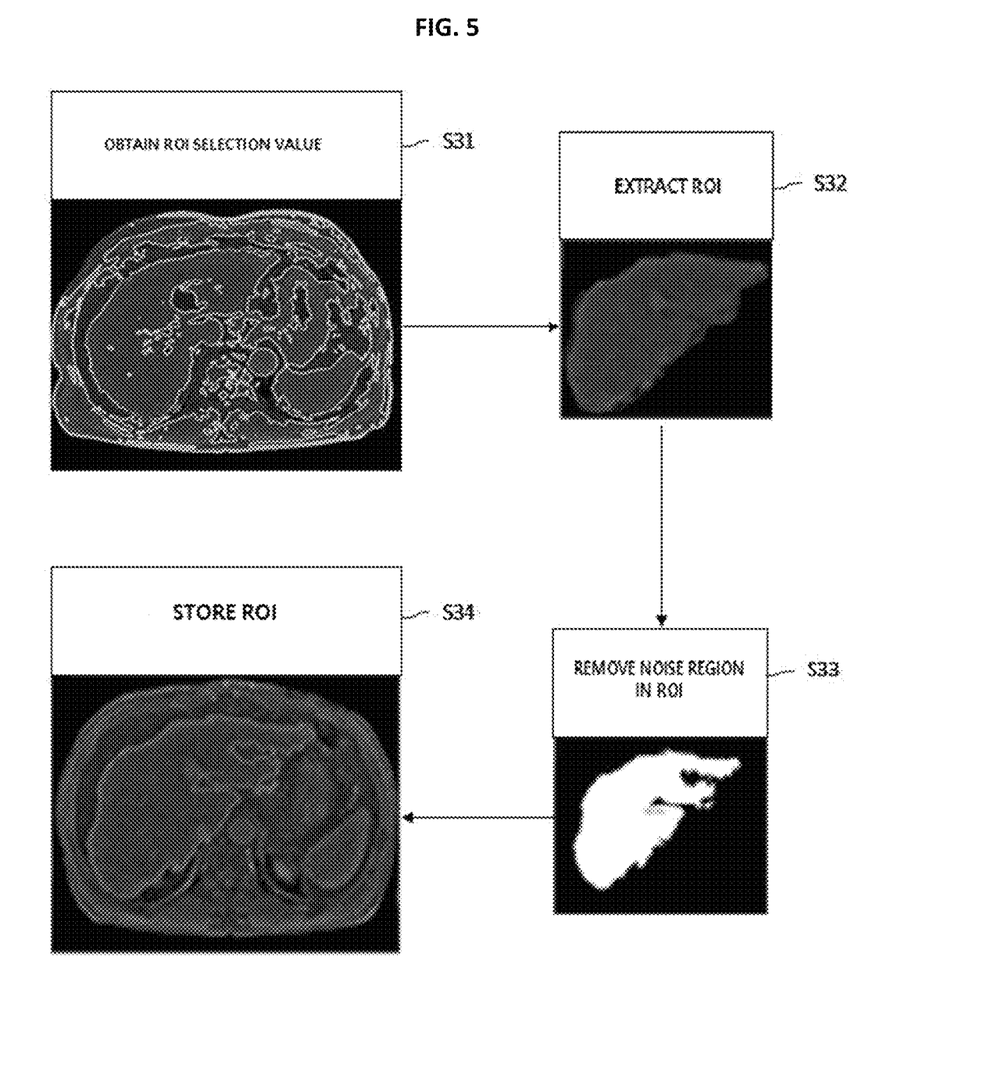
FIG. 5 is a detailed flowchart for illustrating a ROI extracting step according to an embodiment of the present disclosure.
Figure 6:
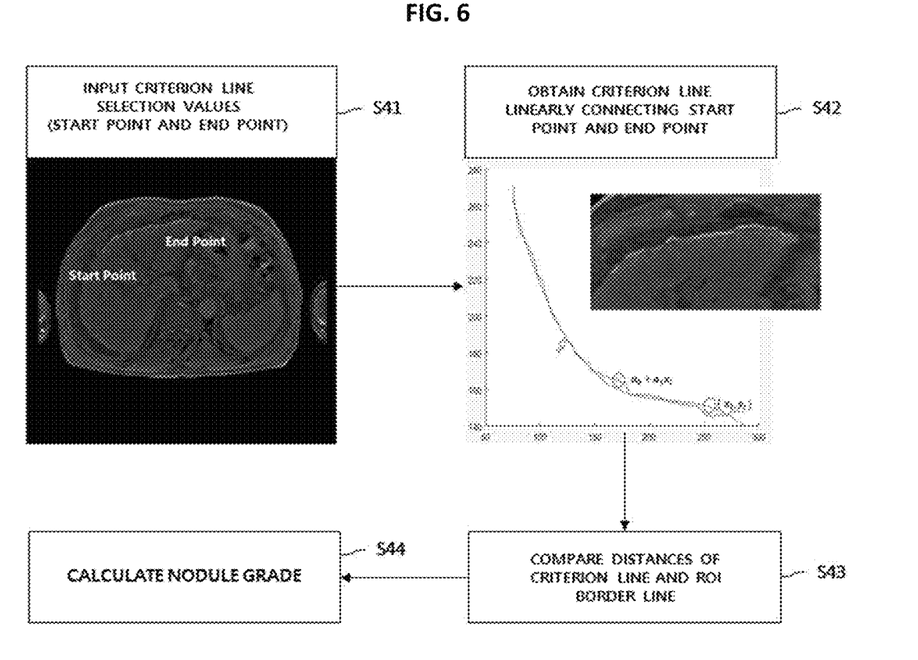
FIGS. 6 and 7 are detailed flowcharts for illustrating a nodule grade calculating step according to an embodiment of the present disclosure.
Figure 7:
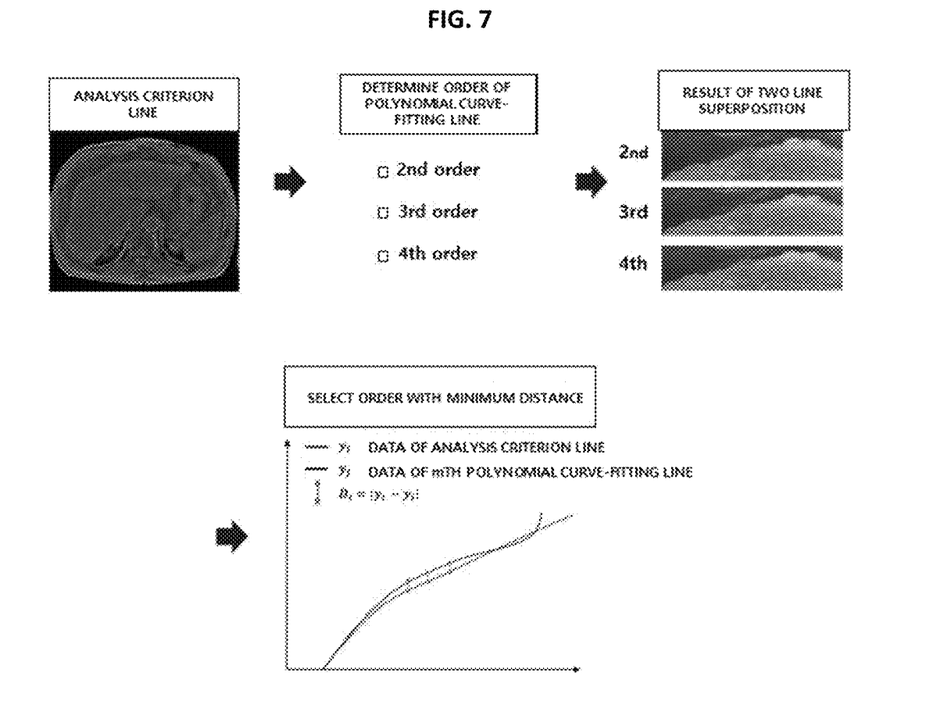
Figure 8:
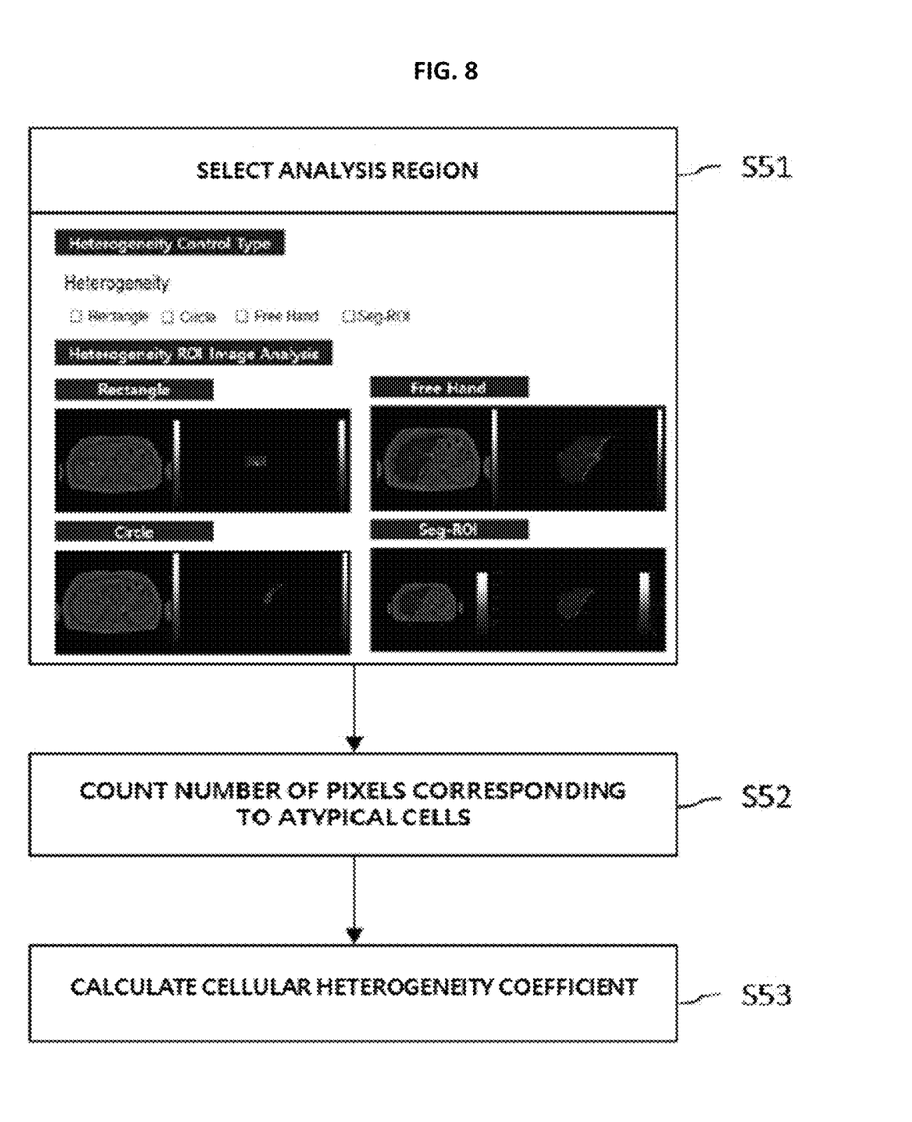
FIG. 8 is a detailed flowchart for illustrating a cellular heterogeneity coefficient calculating step according to an embodiment of the present disclosure.

FIG. 3 is a flowchart for illustrating a whole abdominal disease analyzing method according to an embodiment of the present disclosure, FIG. 4 is a detailed flowchart for illustrating a medical image preprocessing step, FIG. 5 is a detailed flowchart for illustrating a ROI extracting step, FIGS. 6 and 7 are detailed flowcharts for illustrating a nodule grade calculating step according to an embodiment of the present disclosure, and FIG. 8 is a detailed flowchart for illustrating a cellular heterogeneity coefficient calculating step.

First, referring to FIG. 3, the method of the present disclosure may include the steps of receiving a medical image obtained by photographing an abdominal region of a patient (S10), preprocessing the medical image (S20), extracting an ROI based on the preprocessed medical image (S30), calculating a nodule grade based on surface unevenness of the ROI (S40), calculating a cellular heterogeneity coefficient based on pixel homogeneity of the ROI (S50), and predicting and outputting the degree of abdominal disease based on the nodule grade and the cellular heterogeneity coefficient (S60).

First, in the medical image receiving step (S10), the abdominal disease analyzing apparatus 100 accesses the medical imaging device 200 to receive at least one medical image provided by the medical imaging device 200 and then selects and stores one of them as an analysis target image (S10). At this time, the medical image may be a CT image, an MRI image, or an ultrasound image, but the kind of the medical image may be variously added or modified later.

In the medical image preprocessing step (S20), as shown in FIG. 4, first, pixel values in the medical image are equalized. That is, the characteristic of a pixel brightness value observed in the image is defined according to Equation 1, and a value at which the image signal inhomogeneity coefficient and the additive noise are minimized is automatically calculated. Ultimately, a value at which the variance of the noise is minimized is calculated to correct the pixel brightness values, respectively, so as to obtain and output a medical image in which the pixel values are equalized (S21).

$$I = bj + n \quad \text{[Equation 1]}$$

At this time, I is an observed image domain, b is an image signal inhomogeneity coefficient, J is a true image domain containing intrinsic physical features per pixel, and n is an additive noise that is a Gaussian noise with an average of 0 (zero).

In order to calculate the image signal inhomogeneity coefficient b, it is assumed that the value b slowly changes on the observed image domain I. Thus, the values b calculated for adjacent pixels have constant values similar to each other. The true image domain J may be represented by a partition constant $\{C_i\}_{i=1}^{N}$ from 1 to N and a partial image domain set $\{\Omega_i\}_{i=1}^{N}$. At this time, the total sum of the partial image domain may be expressed as $\Omega = \cup_{i=1}^{N} \Omega_i$, $\Omega_i \cap \Omega_j = \emptyset$ when $i \neq j$. Under the above assumption, calculation is repeated ten or more times in order to find a value at which the Gaussian noise n is relatively minimized.

In the ROI extracting step (S30), as shown in FIG. 5, a first input window is provided for allowing a user to manually select the ROI based on the above contour detection result, and a ROI selection value is input through the first input window (S31). For example, a user may manually select an ROI by dragging and dropping a cursor provided by an interface means.

In addition, after a contour having the highest similarity with the ROI selection value is detected, a region located inside the corresponding contour is extracted as the ROI (S32). In addition, the image of interest is binarized and then closed to remove all noise regions included in the image of interest (S33), and the information thereon is stored (S34).

In the nodule grade calculating step (S40), as shown in FIG. 6, a second input window for allowing to select a part of the contour lines of the ROI as an analysis criterion line is provided, and the analysis criterion line (a green line in FIG. 6) is selected and stored based on a start point and an end point input through the second input window (S41).

After that, a polynomial curve-fitting line (using a regression analysis method) corresponding to the analysis criterion line is generated through a regression analysis method. Then, the analysis criterion line and the polynomial curve-fitting line are superimposed on each other, and then points of the two lines are corresponded in one-to-one relationship to calculate a distance therebetween (S42).

At this time, the curve-fitting line may have a second order, a third order or a fourth order. In the present disclosure, as shown in FIG. 7, a $m^{th}$ order polynomial expression corresponding to the analysis criterion line is defined as in Equation 2. After that, the polynomial order (m) in which the square sum of errors (Sr) between the two lines is minimized is calculated, ad this order is selected as the order of the curve-fitting line.

Data of the analysis criterion line $y_i = x_i$

Data of the $m^{th}$ order polynomial curve-fitting line
$y_j = \alpha_0 + \alpha_1 x_i + \alpha_2 x_i^2 + \ldots + \alpha_m x_i^m$ Distance between two lines at the same $x_i$ coordinate location $D_i = |y_i - y_j|$ [Equation 2]

In addition, a distance average value between two lines corresponding to the contour line data (a red line) about a nodule-concerned region and the curve fitting (a blue line) according to the polynomial expression is calculated (S43), and the nodule grade is calculated based on the distance average value (S44).

[Equation 3]

Nodule grade (distance average value, average)

$$\overline{X} = \frac{Score_{nodule}}{n} = \frac{1}{n} \sum_{i=1}^{n} D_i$$

In the cellular heterogeneity coefficient calculating step (S50), a third input window is provided for allowing the user to select a part or all of the ROI as an analysis region, and the analysis region is selected based on an analysis region selection value input through the third input window (S51). For example, the user may manually select the analysis region by dragging and dropping the cursor provided by the interface means.

In addition, atypical cells in the analysis region based on the pixel brightness value is calculated in percentage to find a difference from a reference value after calculating a relative standard deviation of the analysis region (namely, based on a value obtained by dividing the standard deviation of the pixels included in the analysis region by the average value of the pixel brightness value) (S52), and the cellular heterogeneity coefficient is visually calculated as an atypical cell region and a normal cell region (S53).

For reference, as shown in FIG. 8, if atypical cells are generated in a human organ such as the liver due to diseases, the brightness values of the atypical cells and the normal cells are greatly changed. Thus, in the present disclosure, the relative standard deviation (cellular heterogeneity coefficient) of the entire analysis region is calculated based on the pixel brightness value. The cellular heterogeneity coefficient of each pixel is visualized to ultimately detect the atypical cell region and the normal cell region, and the cellular heterogeneity is evaluated based thereon. The cell heterogeneity coefficient is calculated using the following equation.

$$S = \sqrt{\frac{1}{n-1} \sum_{i=1}^{n} (x_i - \overline{x})^2} \quad \text{[Equation 4]}$$

Wherein, S is a standard deviation of pixel values, n is the number of pixels, $x_i$ is the brightness value of an $i^{th}$ pixel, and $\bar{x}$ is an average of pixel brightness values.

$$RS = \frac{S}{\bar{x}} S100 \qquad \text{[Equation 5]}$$

The relative standard deviation of the entire analysis region is expressed by the above equation, and the calculated value RS is used as a reference value to calculate a local cellular heterogeneity coefficient. Wherein, RS is a relative standard deviation, S is a standard deviation of pixel values, and $\bar{x}$ is an average of pixel brightness values.

$$RS'_i = \frac{S}{x_i} S100 \qquad \text{[Equation 6]}$$

The cellular heterogeneity coefficient of the local $i^{th}$ pixel is as shown above. Wherein, $RS'_i$ is a relative standard deviation value the $i^{th}$ pixel, S is a standard deviation of pixel values in the entire analysis region, and $x_i$ is a brightness value of the $i^{th}$ pixel.

In the step of estimating the degree of abdominal disease (S60), analysis criterion information in which correlations of the nodule grade, the cellular heterogeneity coefficient and the degree of abdominal disease are defined is acquired and stored in advance, and the abdominal disease corresponding to the calculated nodule grade and the calculated cellular heterogeneity coefficient (for example, normal, hepatitis, liver cirrhosis, and liver cancer status) is figured out and output.

At this time, the analysis criterion information may be the result of machine learning of nodule grades and cellular heterogeneity coefficients of abdominal disease patients and normal persons, or may be the result of collecting and statistical analyzing previous medical results for each abdominal disease.

For example, it is possible to determine as a normal state if the nodule grade is "1.3" or below and the cellular heterogeneity coefficient is "7.55" or below, as a liver cirrhosis if the nodule grade is "1.5 to 2.5" and the cellular heterogeneity coefficient is "7.56 to 8.80", and as liver cancer if the nodule grade is "2.5" or above and the cellular heterogeneity coefficient is "8.80" or above.

The above description is merely illustrative of the technical idea of the present disclosure, and it will be understood by those skilled in the art that various changes and modifications may be made without departing from the essential characteristics of the present disclosure. Accordingly, the embodiments in the present disclosure are intended to illustrate the technical idea of the present disclosure without limiting the same, and the scope of the technical idea of the present disclosure is not limited by the embodiments. The scope of the present disclosure is to be construed in accordance with the appended claims, and all technical ideas within the scope equivalent thereto shall be construed as falling into the scope of the present disclosure.

What is claimed is:

1. A method for calculating abdominal disease diagnosis information based on a medical image, the method comprising:
receiving a medical image obtained by photographing an abdominal region of a patient to detect a plurality of analysis candidate regions;
preprocessing the medical image by equalizing pixel values in the medical image;
setting at least one of the plurality of analysis candidate regions as a region of interest (ROI) to input an ROI selection value;
extracting the ROI;
calculating a nodule grade based on surface unevenness of the ROI, the calculating comprising:
selecting and storing a part of the contour lines of the ROI as an analysis criterion line;
generating a polynomial curve-fitting line corresponding to the analysis criterion line through a regression analysis method;
superimposing the analysis criterion line and the polynomial curve-fitting line on each other;
corresponding points of the analysis criterion line and the polynomial curve-fitting line in one-to-one relationship to calculate a distance therebetween;
defining a $m^{th}$ order polynomial expression corresponding to the analysis criterion line;
calculating the polynomial order in which the square sum of errors between the analysis criterion line and the polynomial curve-fitting line is minimized and selecting the calculated polynomial order (m) as an order of the curve-fitting line;
calculating a distance average value between the analysis criterion line and the polynomial curve-fitting line corresponding to the contour line data about a nodule-concerned region and a curve fitting according to the polynomial expression; and
calculating the nodule grade on the basis of the distance average value;
calculating a cellular heterogeneity coefficient based on pixel homogeneity of the ROI; and
predicting and outputting an abdominal disease value based on the nodule grade and the cellular heterogeneity coefficient.

2. The method according to claim 1, wherein the step of calculating a cellular heterogeneity coefficient includes:
selecting a partial or entire region of the ROI as an analysis target region based on a user input value; and
calculating a cellular heterogeneity coefficient based on brightness values of pixels in the analysis target region.

3. An apparatus for analyzing an abdominal disease based on a medical image, comprising:
a medical image preprocessing unit configured to detect a plurality of analysis candidate regions by receiving and preprocessing a medical image obtained by photographing an abdominal region of a patient;
a region of interest (ROI) selecting unit configured to set one of the plurality of analysis candidate regions as a ROI;
a nodule grade calculating unit configured to:
select and store a part of the contour lines of the ROI as an analysis criterion line;
generate a polynomial curve-fitting line corresponding to the analysis criterion line through a regression analysis method;
superimpose the analysis criterion line and the polynomial curve-fitting line on each other;
correspond points of the analysis criterion line and the polynomial curve-fitting line in one-to-one relationship to calculate a distance therebetween;
define a $m^{th}$ order polynomial expression corresponding to the analysis criterion line;
calculate the polynomial order in which the square sum of errors between the analysis criterion line and the polynomial curve-fitting line is minimized and selecting the calculated polynomial order (m) as an order of the curve-fitting line;

calculate a distance average value between the analysis criterion line and the polynomial curve-fitting line corresponding to the contour line data about a nodule-concerned region and a curve fitting according to the polynomial expression; and calculate the nodule grade on the basis of the distance average value;

a cellular heterogeneity coefficient calculating unit configured to calculate a cellular heterogeneity coefficient based on pixel homogeneity of the ROI; and a disease analyzing unit configured to predict and output the degree of abdominal disease based on the nodule grade and the cellular heterogeneity coefficient.

4. The method of claim 1, wherein the equalizing comprises finding a value at which the Gaussian noise is minimized in Equation 1:

$$I = bJ + n \quad \text{[Equation 1]}$$

wherein I is an observed image domain, b is an image signal inhomogeneity coefficient, J is a true image domain containing intrinsic physical features per pixel, and n is an additive noise that is the Gaussian noise with an average of 0 (zero).

5. The method of claim 1, wherein the extracting comprises detecting a contour having the highest similarity with the ROI selection value, extracting a region located inside the contour, and removing noise regions included in the ROI by binarizing the ROI.

6. The method according to claim 1, wherein the step of calculating a cellular heterogeneity coefficient comprises:

selecting a part or all of the ROI as an analysis region;

calculating atypical cells in the analysis region based on a pixel brightness value in percentage to find a difference from a reference value after calculating a relative standard deviation of the analysis region; and calculating the cellular heterogeneity coefficient as an atypical cell region and a normal cell region.

7. A method for calculating abdominal disease diagnosis information based on a medical image, the method comprising:

receiving a medical image obtained by photographing an abdominal region of a patient to detect a plurality of analysis candidate regions;

preprocessing the medical image by equalizing pixel values in the medical image, the equalizing comprised of:

finding a value at which the Gaussian noise is minimized in Equation 1:

$$I = bJ + n \quad \text{[Equation 1]}$$

wherein I is an observed image domain, b is an image signal inhomogeneity coefficient, J is a true image domain containing intrinsic physical features per pixel, and n is an additive noise that is the Gaussian noise with an average of 0 (zero);

setting at least one of the plurality of analysis candidate regions as a region of interest (ROI) to input an ROI selection value;

extracting the ROI, the extracting comprising detecting a contour having the highest similarity with the ROI selection value, extracting a region located inside the contour, and removing noise regions included in the ROI by binarizing the ROI;

calculating a nodule grade based on surface unevenness of the ROI, the calculating comprising:

selecting and storing a part of the contour lines of the ROI as an analysis criterion line;

generating a polynomial curve-fitting line corresponding to the analysis criterion line through a regression analysis method;

superimposing the analysis criterion line and the polynomial curve-fitting line on each other;

corresponding points of the analysis criterion line and the polynomial curve-fitting line in one-to-one relationship to calculate a distance therebetween;

defining a $m^{th}$ order polynomial expression corresponding to the analysis criterion line;

calculating the polynomial order in which the square sum of errors between the analysis criterion line and the polynomial curve-fitting line is minimized and selecting the calculated polynomial order (m) as an order of the curve-fitting line;

calculating a distance average value between the analysis criterion line and the polynomial curve-fitting line corresponding to the contour line data about a nodule-concerned region and a curve titling according to the poi normal expression; and calculating the nodule grade on the basis of the distance average value;

calculating a cellular heterogeneity coefficient based on pixel homogeneity of the ROI by selecting a part or all of the ROI as an analysis region, calculating atypical cells in the analysis region based on a pixel brightness value in percentage to find a difference from a reference value after calculating a relative standard deviation of the analysis region, and calculating the cellular heterogeneity coefficient as an atypical cell region and a normal cell region; and predicting and outputting an abdominal disease value based on the nodule grade and the cellular heterogeneity coefficient.

* * * * *